(12) United States Patent
Takemoto

(10) Patent No.: US 10,500,144 B2
(45) Date of Patent: Dec. 10, 2019

(54) PHOTOCURABLE COMPOSITION TO BE USED ON FINGERNAILS OR ARTIFICIAL NAILS, AND METHOD FOR COATING BY USING SAME

(71) Applicant: THREE BOND CO., LTD., Tokyo (JP)

(72) Inventor: Koichi Takemoto, Tokyo (JP)

(73) Assignee: THREE BOND CO., LTD., Tokyo (JP)

( * ) Notice: Subject to any disclaimer, the term of this patent is extended or adjusted under 35 U.S.C. 154(b) by 0 days.

(21) Appl. No.: 15/774,415

(22) PCT Filed: Oct. 26, 2016

(86) PCT No.: PCT/JP2016/081780
§ 371 (c)(1),
(2) Date: May 8, 2018

(87) PCT Pub. No.: WO2017/082058
PCT Pub. Date: May 18, 2017

(65) Prior Publication Data
US 2018/0325789 A1 Nov. 15, 2018

(30) Foreign Application Priority Data
Nov. 9, 2015 (JP) ................................. 2015-219347

(51) Int. Cl.
| | |
|---|---|
| A61K 8/42 | (2006.01) |
| A61Q 3/02 | (2006.01) |
| A61K 8/35 | (2006.01) |
| A61K 8/36 | (2006.01) |
| A61K 8/49 | (2006.01) |
| A61K 8/55 | (2006.01) |
| A61K 8/87 | (2006.01) |
| C08F 2/50 | (2006.01) |
| C08F 220/06 | (2006.01) |
| C08F 220/18 | (2006.01) |
| C08F 220/56 | (2006.01) |
| A45D 31/00 | (2006.01) |
| B05D 3/10 | (2006.01) |
| B05D 7/24 | (2006.01) |
| C09D 5/00 | (2006.01) |
| C08F 242/00 | (2006.01) |
| C09D 193/04 | (2006.01) |
| C09D 7/40 | (2018.01) |

(52) U.S. Cl.
CPC ................ *A61K 8/42* (2013.01); *A45D 31/00* (2013.01); *A61K 8/35* (2013.01); *A61K 8/36* (2013.01); *A61K 8/49* (2013.01); *A61K 8/55* (2013.01); *A61K 8/87* (2013.01); *A61Q 3/02* (2013.01); *B05D 3/10* (2013.01); *B05D 7/24* (2013.01); *C08F 2/50* (2013.01); *C08F 220/06* (2013.01); *C08F 220/18* (2013.01); *C08F 220/56* (2013.01); *C08F 242/00* (2013.01); *C09D 5/00* (2013.01); *C09D 193/04* (2013.01); *C09D 7/40* (2018.01)

(58) Field of Classification Search
None
See application file for complete search history.

(56) References Cited

U.S. PATENT DOCUMENTS

| | | | | |
|---|---|---|---|---|
| 5,948,419 A | * | 9/1999 | Bankert | ................. A61K 8/585 424/401 |
| 2003/0073753 A1 | | 4/2003 | Lilley et al. | |
| 2014/0030199 A1 | * | 1/2014 | Matsumoto | ............... A61K 8/37 424/61 |
| 2014/0309327 A1 | | 10/2014 | Nogami et al. | |
| 2016/0184213 A1 | | 6/2016 | Abe | |

FOREIGN PATENT DOCUMENTS

| | | | |
|---|---|---|---|
| JP | 2005-118398 A | 5/2005 | |
| JP | 2014-23590 A | 2/2014 | |
| PL | 407155 A1 * | 8/2015 | |
| WO | WO-0028948 A1 * | 5/2000 | ............... A61K 8/91 |
| WO | 2000/76366 A1 | 12/2000 | |
| WO | 2013/073364 A1 | 5/2013 | |
| WO | 2015/046300 A1 | 4/2015 | |
| WO | 2015/163353 A1 | 10/2015 | |

OTHER PUBLICATIONS

International Search Report dated Feb. 7, 2017 of corresponding International Application No. PCT/JP2016/081780; 7 pgs.
International Preliminary Report on Patentability dated May 24, 2018 of corresponding International Application No. PCT/JP2016/081780; 22 pgs.

* cited by examiner

*Primary Examiner* — Robert A Wax
*Assistant Examiner* — Melissa S Mercier
(74) *Attorney, Agent, or Firm* — Maier & Maier, PLLC

(57) ABSTRACT

A photocurable composition for a nail or artificial nail which can form a cured product exhibiting excellent durability (adhesion maintainability to nails). In addition, the present invention provides a photocurable composition for a nail or artificial nail which emits a weaker odor, generates less heat at the time of curing, and can form a cured product exhibiting excellent surface curability. In addition, the present invention provides a photocurable composition for nail or artificial nail which can form a cured product having an excellent shear adhesive force. The photocurable composition for nail or artificial nail according to the present invention contains the following components (A) to (D): component (A): a urethane-modified (meth)acrylic oligomer; component (B): a (meth)acrylamide monomer; component (C): a (meth)acrylic monomer having an acidic group; and component (D): a photoinitiator.

7 Claims, No Drawings

PHOTOCURABLE COMPOSITION TO BE USED ON FINGERNAILS OR ARTIFICIAL NAILS, AND METHOD FOR COATING BY USING SAME

FIELD

The present invention relates to a photocurable composition for nail or artificial nail and a covering method using the same. The present invention particularly relates to a photocurable composition for nail or artificial nail to be suitably used as abase coat agent in the field of nails and a method of covering a human nail or an artificial nail using the same.

BACKGROUND

Hitherto, in the field of nails, coating layers have been formed on a nail in multiple layers. Specifically, a base coat agent is applied on the nail to forma coating layer and then a photocurable composition (UV nail gel) is further applied thereon. A solvent-based base coat agent containing nitrocellulose as a main component is disclosed in WO 2000-076366 A1. In addition, a photocurable artificial nail composition which is a base coat agent is disclosed in JP 2014-23590 A (corresponding to US 2014/030199 A).

SUMMARY OF INVENTION

However, the base coat agent disclosed in WO 2000-076366 A1 has drawbacks that it takes a long time to dry the base coat agent (namely, poor surface curability) and the base coat agent has an odor. In addition, the photocurable composition disclosed in JP 2014-23590 A (corresponding to US 2014/030199 A) generates heat when being irradiated with UV for curing, and thus it has a problem when being applied to a base coat agent to be directly applied on the nail. Furthermore, the base coat (cured product) to be formed from such a composition is brought into direct contact with the nail, and thus moisture remains at the interface by perspiration from the nail, bathing, dishwashing, and the like, peeling off occurs between the nail and the base coat in some cases, and a secondary problem such as generation of fungi at the peeled off portion is also caused. Hence, the base coat is required to exhibit durability (adhesion maintainability to nails) in everyday life.

Accordingly, an object of the present invention is to provide a photocurable composition for nail or artificial nail which can form a cured product exhibiting excellent durability (adhesion maintainability to nails). Another object of the present invention is to provide a photocurable composition for nail or artificial nail which emits a weaker odor, generates less heat at the time of curing, and can form a cured product exhibiting excellent surface curability. Still another object of the present invention is to provide a photocurable composition for nail or artificial nail which can form a cured product having an excellent shear adhesive force. Yet another object of the present invention is to provide a covering method using the photocurable composition.

The photocurable composition for nail or artificial nail of the present invention and the covering method using the same in order to achieve the above objects have the following configurations.

1. A photocurable composition for nail or artificial nail including the following components (A) to (D):
  component (A): a urethane-modified (meth)acrylic oligomer;
  component (B): a (meth)acrylamide monomer;
  component (C): a (meth)acrylic monomer having an acidic group; and
  component (D): a photoinitiator.

2. The photocurable composition for nail or artificial nail according to 1, wherein the component (A) is a urethane-modified (meth)acrylic oligomer having two (meth)acryl groups in one molecule.

3. The photocurable composition for nail or artificial nail according to 1 or 2, wherein the component (B) is contained at from 15 to 50 parts by mass with respect to 100 parts by mass of the component (A) and the component (C) is contained at from 1 to 10 parts by mass with respect to 100 parts by mass of the component (A).

4. The photocurable composition for nail or artificial nail according to any one of 1 to 3, wherein the component (B) is at least either of 4-acryloylmorpholine or dialkylacrylamide.

5. The photocurable composition for nail or artificial nail according to any one of 1 to 4, wherein the component (C) is (meth)acrylic acid.

6. The photocurable composition for nail or artificial nail according to any one of 1 to 5, further including a silane-based coupling agent.

7. A method of covering a human nail or an artificial nail, the method including applying the photocurable composition for nail or artificial nail according to any one of 1 to 6 on a human nail or an artificial nail to form a layer and then irradiating the layer with an energy ray for curing.

8. The photocurable composition for nail or artificial nail according to any one of 1 to 6, wherein the photocurable composition for nail or artificial nail is a base coat agent.

DETAILED DESCRIPTION

The photocurable composition for nail or artificial nail according to the present invention (hereinafter also referred to as a "photocurable composition" or simply a "composition") contains a component (A): a urethane-modified (meth)acrylic oligomer, a component (B): a (meth)acrylamide monomer, a component (C): a (meth)acrylic monomer having an acidic group, and a component (D): a photoinitiator.

The composition can form a cured product (base coat) exhibiting excellent durability (adhesion maintainability to nails). In addition, the composition emits a weaker odor, generates less heat at the time of curing, and can form a cured product exhibiting excellent surface curability. Furthermore, the composition can forma cured product having an excellent shear adhesive force.

It is preferable that the photocurable composition for nail or artificial nail is a photocurable composition for covering nail or artificial nail.

Hereinafter, the composition of the present invention will be described in detail.

Incidentally, in the present specification, "X to Y" is used in the meaning to include the numerical values (X and Y) described before and after it as the lower limit value and the upper limit value. In addition, unless otherwise specified, the operation and measurement of physical properties and the like are conducted under the conditions of room temperature (20° C. to 25° C.)/relative humidity of 40 to 50%.

In addition, in the present specification, the term "(meth)acryl" means acryl and/or methacryl.

<Constituent of Composition>

[Component (A)]

The component (A) of the composition according to the present invention is a urethane-modified (meth)acrylic oligomer. It is preferable that the component (A) is liquid at 25° C. (that is, it exhibits fluidity at 25° C.) from the viewpoint of ease of handling. In addition, it is preferable that the component (A) has 2 or more and 10 or fewer (meth)acryl groups in one molecule from the viewpoint of increasing the curing rate of the composition and the toughness of the cured product to be formed. Among these, it is more preferable to have two (meth)acryl groups in one molecule since the shear adhesive force is improved while the cured product does not become too brittle. As the component (A), it is preferable to use one which exhibits favorable compatibility with the components (B) to (D) of the present invention.

The weight average molecular weight of the component (A) is preferably 500 or more and 50000 or less and more preferably 500 or more and 30000 or less. The strength of the cured product and the followability thereof to nails are in a favorable balance when the weight average molecular weight is in such a range. Incidentally, in the present specification, a value measured by gel permeation chromatography (GPC) using polystyrene as a standard substance is adopted as the weight average molecular weight.

As the urethane-modified (meth)acrylic oligomer, a compound synthesized by reacting a polyol having an ester bond, an ether bond, a polycarbonate bond, a bisphenol skeleton, a hydrogenated bisphenol skeleton, or the like in the molecule with a polyisocyanate to form a urethane bond and adding a compound having a hydroxyl group and a (meth) acryl group in the molecule or (meth)acrylic acid to the remaining isocyanate group, and the like are known.

As the component (A), either a commercially available product or a synthetic product may be used. Specific examples of the commercially available product may include AH-600, AT-600, UA-306H, UF-8001G, and the like manufactured by KYOEISHA CHEMICAL CO., LTD., but it is not limited thereto. Incidentally, the component (A) may be used singly or two or more kinds thereof may be used concurrently.

[Component (B)]

The component (B) of the composition according to the present invention is a (meth)acrylamide monomer. The durability (adhesion maintainability to nails) of the cured product to be formed remarkably decreases in a case in which the composition does not contain the component (B) (see Comparative Examples 1 to 7). As the reason for this, it is considered that a composition which does not contain the component (B) hardly forms a hard cured product and thus the cured product to be formed is likely to be affected by humidity although it is not particularly limited thereto. From the viewpoint of workability, it is preferable that the component (B) is liquid at 25° C. (that is, it exhibits fluidity at 25° C.), and specifically, the viscosity at 25° C. is preferably about 500 mPa·s or less.

Specific examples of the component (B) may include (meth)acrylamide, N-methyl(meth)acrylamide, N-ethyl (meth)acrylamide, N-propyl(meth)acrylamide, N-n-butyl (meth)acrylamide, N-tert-butyl(meth)acrylamide, N-butoxymethyl(meth)acrylamide, N-isopropyl(meth) acrylamide, N-methylol (meth)acrylamide, N,N-dimethyl (meth)acrylamide, (meth)acryloylmorpholine, N,N-diethyl (meth)acrylamide, N-methyl-N-ethyl(meth)acrylamide, and N-hydroxyethyl(meth)acrylamide, but it is not limited thereto. Among these, the component (B) is preferably at least either of acryloylmorpholine or dialkylacrylamide from the viewpoint of forming a harder cured product. Here, "alkyl" refers to a linear or branched C1 to C4 alkyl such as methyl, ethyl, n-propyl, isopropyl, n-butyl, or the like. N,N-diethylacrylamide or N,N-dimethylacrylamide is preferable when the price and ease of availability are taken into consideration. It is particularly preferable that the component (B) contains N,N-dimethylacrylamide from the viewpoint of further enhancing the durability (adhesion maintainability to nails) in everyday use. These may be used singly or two or more kinds thereof may be used concurrently.

As the component (B), either of a commercially available product or a synthetic product may be used. As specific examples of the commercially available product, DMAA (registered trademark), ACMO (registered trademark), DEAA (registered trademark), and the like manufactured by KJ Chemicals Corporation and the like are known, but it is not limited thereto.

The content of the component (B) in the composition of the present invention is preferably from 1 to 50 parts by mass, more preferably from 15 to 50 parts by mass, still more preferably from 20 to 40 parts by mass, and particularly preferably from 25 to 35 parts by mass with respect to 100 parts by mass of the component (A). The coating property and the adhesive force are favorable when the component (B) is 1 part by mass or more. Meanwhile, it is possible to maintain the surface curability when being irradiated with light when the component (B) is 50 parts by mass or less.

[Component (C)]

The component (C) of the composition according to the present invention is a (meth)acrylic monomer having an acidic group. The durability and shear adhesive force of the cured product to be formed remarkably decrease in a case in which the composition does not contain the component (C) (see Comparative Example 8). The reason for this is not particularly limited, but it is considered that the cured product to be formed from the composition which does not contain the component (C) exhibits poor adhesive property at the interface with the adherend and thus a large amount of moisture is likely to be present at the interface. The acidic group is not particularly limited, and examples thereof may include a carboxyl group, a phosphoric acid group, a sulfonic acid group, and groups of salts thereof. Among these, the acidic group is preferably a carboxyl group or a group of a salt thereof from the viewpoint of further improving the adhesive property.

Examples of the (meth)acrylic monomer having a carboxyl group as specific examples of the component (C) may include (meth)acrylic acid, 3-(meth)acryloyloxypropylsuccinic acid, 4-(meth)acryloyloxybutylsuccinic acid, 2-(meth) acryloyloxyethylmaleic acid, 3-(meth)acryloyloxypropylmaleic acid, 4-(meth)acryloyloxybutylmaleic acid, 2-(meth) acryloyloxyethylhexahydrophthalic acid, 3-(meth) acryloyloxypropylhexahydrophthalic acid, 4-(meth) acryloyloxybutylhexahydrophthalic acid, 2-(meth) acryloyloxyethylphthalic acid, 3-(meth) acryloyloxypropylphthalic acid, and 4-(meth) acryloyloxybutylphthalic acid. Examples of the (meth) acrylic monomer having a phosphoric acid group may include 2-ethylhexyl acid phosphate, 2-hydroxyethyl methacrylate acid phosphate, and dibutyl phosphate, but it is not limited thereto. When the influence on the skin is taken into consideration, (meth)acrylic acid is preferable and methacrylic acid is more preferable. These may be used singly or two or more kinds thereof may be used concurrently.

The content of the component (C) in the composition of the present invention is preferably from 1 to 20 parts by mass, more preferably from 1 to 10 parts by mass, still more preferably from 2 to 8 parts by mass, and particularly preferably from 3 to 6 parts by mass with respect to 100 parts by mass of the component (A). It is possible to maintain the adhesive force when the component (C) is 1 part by mass or more. Meanwhile, it is possible to decrease skin irritation when the component (C) is 20 parts by mass or less.

In other words, a preferred embodiment of the present invention is a photocurable composition for nail or artificial nail, which contains the component (B) at from 15 to 50 parts by mass with respect to 100 parts by mass of the component (A) and the component (C) at from 1 to 10 parts by mass with respect to 100 parts by mass of the component (A). The effect of the present invention is further improved by the synergistic effect of the component (B) and the component (C) when the component (B) and the component (C) are contained in such ranges.

[Component (D)]

The component (D) of the composition according to the present invention is a photoinitiator and is not limited as long as it is a radical photoinitiator which generates radical species by energy rays such as visible light, ultraviolet light, X-ray, and an electron beam.

Specific examples of the component (D) may include acetophenones such as diethoxyacetophenone, 2-hydroxy-2-methyl-1-phenylpropan-1-one, benzyl dimethyl ketal, 4-(2-hydroxyethoxy)phenyl-(2-hydroxy-2-propyl)ketone, 1-hydroxycyclohexyl phenyl ketone (Suncure 84), 2-methyl-2-morpholino(4-thiomethylphenyl)propane-1-one, 2-benzyl-2-dimethylamino-1-(4-morpholinophenyl)butanone, and a 2-hydroxy-2-methyl-1-[4-(1-methylvinyl)phenyl]propanone oligomer; benzoins such as benzoin, benzoin methyl ether, benzoin ethyl ether, benzoin isopropyl ether, and benzoin isobutyl ether; benzophenones such as benzophenone, methyl o-benzoylbenzoate, 4-phenylbenzophenone, 4-benzoyl-4'-methyl-diphenylsulfide, 3,3',4,4'-tetra(t-butylperoxycarbonyl)benzophenone, 2,4,6-trimethylbenzophenone, 4-benzoyl-N,N-dimethyl-N-[2-(1-oxo-2-propenyloxy)ethyl]b enzenemethanaminium bromide, and (4-benzoylbenzyl)trimethylammonium chloride; and thioxanthones such as 2-isopropylthioxanthone, 4-isopropylthioxanthone, 2,4-diethylthioxanthone, 2,4-dichlorothioxanthone, 1-chloro-4-propoxythioxanthone, and 2-(3-dimethylamino-2-hydroxy)-3,4-dimethyl-9H-thioxanthone-9-one mesochloride, but it is not limited thereto. These may be used singly or two or more kinds thereof may be used concurrently.

The content of the component (D) in the composition of the present invention is preferably from 0.1 to 20 parts by mass, more preferably from 1 to 10 parts by mass, still more preferably from 2 to 8 parts by mass, and particularly preferably from 3 to 7 parts by mass with respect to 100 parts by mass of the component (A). It is possible to maintain the photocurability when the component (D) is 0.1 parts by mass or more. Meanwhile, it is possible to maintain the storage stability without causing thickening at the time of storage when the component (D) is 20 parts by mass or less.

It is preferable that the component (D) contains a visible light type photoinitiator. The content of the visible light type photoinitiator in the composition of the present invention is preferably from 0 to 70% by mass, more preferably from 20 to 60% by mass, and still more preferably from 40 to 58% by mass with respect to the mass of the entire component (D). Yellowing of the cured product hardly occurs when the content is in such a range. In addition, the composition exhibits excellent surface curability when the content is in such a range. Here, the visible light type photoinitiator is a photoinitiator having an absorption maximum in the visible light region (wavelength range of from 400 to 800 nm and preferably from 400 to 500 nm) and mainly refers to an acylphosphine oxide-based photopolymerization initiator containing a phosphorus atom. Specific examples of the acylphosphine oxide-based photopolymerization initiator containing a phosphorus atom may include 2,4,6-trimethyl-benzoyl-diphenyl-phosphine oxide (LUCIRIN (registered trademark) TPO) and bis(2,4,6-trimethylbenzoyl)-phenyl-phosphine oxide, but it is not limited thereto. These may be used singly or two or more kinds thereof may be used concurrently.

[Silane-Based Coupling Agent]

It is preferable that the composition according to the present invention further contains a silane-based coupling agent from the viewpoint of further improving the adhesive property. Examples of the silane-based coupling agent may include a silane-based coupling agent having an epoxy group, a vinyl group, an acrylic group, or a methacrylic group and a hydrolyzable silyl group (for example, an alkoxysilyl group such as a methoxysilyl group or an ethoxysilyl group), a polyorganosiloxane having a phenyl group and a hydrolyzable silyl group, and a polyorganosiloxane having an epoxy group and a hydrolyzable silyl group, but it is not limited thereto. Specific examples of the silane-based coupling agent may include allyltrimethoxysilane, vinyltrimethoxysilane, 3-glycidoxypropyltrimethoxysilane, 3-methacryloxypropyltrimethoxysilane, 3-acryloxypropyltrimethoxysilane, and 3-chloropropyltrimethoxysilane, but it is not limited thereto. These may be used singly or two or more kinds thereof may be used concurrently.

In a case in which the composition according to the present invention contains a silane-based coupling agent, the content thereof is preferably from 0.1 to 10 parts by mass, more preferably from 0.5 to 5 parts by mass, and still more preferably from 1 to 3 parts by mass with respect to 100 parts by mass of the component (A).

[Filler]

It is preferable that the composition according to the present invention further contains a filler such as an inorganic filler or an organic filler. It is possible to adjust not only the viscosity and thixotropy but also curability and toughness by adding a filler. Examples of the inorganic filler may include alumina, silica, and amorphous silica, but it is not limited thereto. Among these, fumed silica is preferable and untreated fumed silica is more preferable. Meanwhile, examples of the organic filler may include a styrene filler, a rubber filler, and a core-shell acrylic filler, but it is not limited thereto.

As the filler, either of a commercially available product or a synthetic product may be used. Examples of the commercially available product may include FUSELEX E-1 manufactured by Tatsumori Ltd. and AO-802 manufactured by Admatechs Company Limited as a silica powder and 200 (not treated), R972 (treated with dimethyldichlorosilane), R976 (treated with dimethyl dichlorosilane), RY200 (treated with dimethyl silicone), RX200 (treated with hexamethyldisilazane), R800 (treated with octylsilane), and the like as AEROSIL series manufactured by NIPPON AEROSIL CO., LTD., but it is not limited thereto. These may be used singly or two or more kinds thereof may be used concurrently.

In a case in which the composition according to the present invention contains a filler, the content thereof is preferably from 0.1 to 5 parts by mass, more preferably from 0.2 to 2 parts by mass, and still more preferably from 0.4 to 1 part by mass with respect to 100 parts by mass of component (A).

[Other (Meth)acrylic Monomers]

The composition according to the present invention may contain (meth)acrylic monomers (other (meth)acrylic monomers) other than the components (B) and (C) described above, and may contain a monofunctional and/or bifunctional(meth)acrylic monomer.

Specific examples of a monofunctional (meth)acrylic monomer may include lauryl(meth)acrylate, stearyl (meth)acrylate, ethyl carbitol (meth)acrylate, tetrahydrofurfuryl (meth)acrylate, caprolactone-modified tetrahydrofurfuryl (meth)acrylate, cyclohexyl (meth)acrylate, dicyclopentanyl (meth)acrylate, isobornyl (meth)acrylate, benzyl (meth)acrylate, phenyl (meth)acrylate, phenoxyethyl (meth)acrylate, phenoxydiethylene glycol (meth)acrylate, phenoxytetraethylene glycol (meth)acrylate, nonylphenoxyethyl (meth)acrylate, nonylphenoxytetraethylene glycol (meth)acrylate, methoxydiethylene glycol (meth)acrylate, ethoxydiethylene glycol (meth)acrylate, butoxyethyl (meth)acrylate, butoxytriethylene glycol (meth)acrylate, 2-ethylhexylpolyethylene glycol (meth)acrylate, 4-hydroxybutyl (meth)acrylate, nonylphenylpolypropylene glycol (meth)acrylate, methoxydipropylene glycol (meth)acrylate, 2-hydroxyethyl (meth)acrylate, 2-hydroxypropyl (meth)acrylate, glycerol (meth)acrylate, polyethylene glycol (meth)acrylate, polypropylene glycol (meth)acrylate, epichlorohydrin-modified butyl (meth)acrylate, epichlorohydrin-modified phenoxy (meth)acrylate, N,N-dimethylaminoethyl (meth)acrylate, and N,N-diethylaminoethyl (meth)acrylate, but it is not limited thereto.

Specific examples of a bifunctional (meth)acrylic monomer may include 1,3-butylene glycol di(meth)acrylate, 1,4-butylene glycol di(meth)acrylate, tricyclodecanedimethanol di(meth)acrylate, neopentyl glycol di (meth)acrylate, 1,6-hexane glycol di(meth)acrylate, ethylene glycol diacrylate, tetraethylene glycol di(meth)acrylate, polyethylene glycol di(meth)acrylate, propylene glycol di(meth)acrylate, tripropylene glycol di(meth)acrylate, ethylene oxide-modified neopentyl glycol di(meth)acrylate, propylene oxide-modified neopentyl glycol di(meth)acrylate, bisphenol A di(meth)acrylate, ethylene oxide-modified bisphenol A di(meth)acrylate, epichlorohydrin-modified bisphenol A di(meth)acrylate, ethylene oxide-modified bisphenol S di(meth)acrylate, neopentyl glycol-modified trimethylolpropane di(meth)acrylate, dicyclopentenyl di(meth)acrylate, ethylene oxide-modified dicyclopentenyl di(meth)acrylate, and diacryloyl isocyanurate, but it is not limited thereto.

In the composition according to the present invention, the content of the other (meth)acrylic monomers is preferably less than 5 parts by mass, more preferably less than 1 part by mass, and still more preferably less than 0.1 parts by mass (lower limit: 0 part by mass) with respect to 100 parts by mass of the component (A). The durability (adhesion maintainability to nails) and shear adhesive force of the cured product are favorable when the content is in such a range.

[Plasticizer]

In the present invention, a plasticizer can be added to an extent to which the properties of the present invention are not impaired. Specific examples of the plasticizer may include aromatic polycarboxylic acid ester as a polycarboxylic acid ester-based plasticizer, dioctyl phthalate (DOP), dibutyl phthalate (DBP), diheptyl phthalate (DHP), diisononyl phthalate (DINP), diisodecyl phthalate (DIDP), butylbenzylphthalate (BBP), and the like as a phthalic acid ester, trioctyl trimellitate (TOTM), triisodecyl trimellitate (TITM), and the like as a trimellitic acid ester, tetraoctyl pyromellitate and the like as a pyromellitic acid ester, di-2-ethylhexyladipate (DOA), isodecyladipate (DIDA), di-2-ethylhexyl sebacate (DOS), dibutyl sebacate (DBS), di-2-ethylhexyl maleate (DOM), dibutyl fumarate (DBF), di-2-ethylhexyl azelate (DOZ), di-2-ethylhexyl epoxy hexahydrophthalate, trioctyl citrate, glycerol triacetate, and the like as an aliphatic polycarboxylic acid ester, but it is not limited thereto. In addition, examples of a phosphoric acid ester-based plasticizer may include trimethyl phosphate, tributylphosphate, tri-(2-ethylhexyl) phosphate, tributoxyethyl phosphate, triphenyl phosphate, tricresyl phosphate, alkylallyl phosphate, triethyl phosphate, tri(chloroethyl) phosphate, tris(dichloropropyl) phosphate, tris(β-chloropropyl) phosphate, octyldiphenyl phosphate, tris(isopropylphenyl) phosphate, and cresylphenylphosphate, but it is not limited thereto. In addition, a plurality of plasticizers can also be used in combination.

In the present invention, additives such as coloring agents such as a pigment and a dye, an antioxidant, a polymerization inhibitor, a defoaming agent, a leveling agent, and a rheology control agent may be blended in appropriate amounts to an extent to which the properties of the present invention are not impaired. By addition of these, a composition which exhibits excellent resin strength, adhesive force, workability, storage stability, and the like or a cured product thereof is obtained.

<Use>

The present invention also provides a method of covering a human nail or an artificial nail, which includes applying the composition according to the present invention on a human nail or an artificial nail to form a layer and then irradiating the layer with an energy ray for curing. Preferred applying and irradiation conditions in the method are as follows. Here, "to be applied on a human nail or an artificial nail" represents that the composition may be applied directly on the surface of a human nail or artificial nail or may be applied on the outermost surface of one or more layers formed on the surface of a human nail or artificial nail. Among these, the composition according to the present invention can be suitably used as a base coat agent to be directly applied on a nail or an artificial nail (particularly a human nail) since it generates less heat when being irradiated with light for curing. In other words, a preferred embodiment of the present invention is the photocurable composition for nail or artificial nail which is a base coat agent. Incidentally, the composition according to the present invention may be used as a covering agent for nail or artificial nail (for example, a top coat agent) other than a base coat agent.

It is preferable that the surface of a human nail or artificial nail is sanded using a file or the like and then the dust, oil, moisture, and the like on the nail are removed using a solvent for nail exclusive use containing ethanol as a main component before applying the composition of the present invention. It is preferable to form a layer having a thickness of about from 100 to 300 μm in a wet state using a brush, a paintbrush, or the like when applying the composition of the present invention. At the time of applying, a primer may be used in advance. As an irradiation apparatus of energy rays (for example, visible light, ultraviolet ray, X-ray, an electron beam, and the like) at the time of curing, it is preferable to use a commercially available UV lamp or LED lamp. The irradiation time is preferably from 10 seconds to 120 seconds, and it is more preferably from 10 seconds to 70 seconds and still more preferably from 10 seconds to 60 seconds when the influence on the finger is taken into consideration. The integrated light quantity is preferably from 5 to 60 kJ/m$^2$.

EXAMPLES

Next, the present invention will be described in more detail with reference to Examples, but the present invention is not limited only to these Examples. Incidentally, in the following Examples, operations were conducted at room temperature (25° C.) unless otherwise specified. In addition, "%" and "parts" mean "% by mass" and "parts by mass", respectively, unless otherwise specified.

Examples 1 and 2 and Comparative Examples 1 to 8

In order to prepare a photocurable composition for nail or artificial nail, the following components were prepared:

[Component (A): Urethane-Modified (Meth)acrylic Oligomer]
Urethane acrylic oligomer (bifunctional, weight average molecular weight: 4500) (UF-8001G manufactured by KYOEISHA CHEMICAL CO., LTD.)

[Component (B): (Meth)acrylamide Monomer]
4-Acryloylmorpholine (ACMO (registered trademark) manufactured by KJ Chemicals Corporation)
N,N-dimethylacrylamide (DMAA (registered trademark) manufactured by KJ Chemicals Corporation)

[(B') Component: Monomer other than Component (B)]
4-Hydroxybutyl acrylate (4HBA manufactured by Nippon Kasei Chemical Co., Ltd.)
2-Hydroxypropyl methacrylate (HPMA manufactured by NIPPON SHOKUBAI CO., LTD.)
Isobornyl acrylate (LIGHT ACRYLATE (registered trademark) IB-XA, manufactured by KYOEISHA CHEMICAL CO., LTD.) (referred to as "IB-XA" in the following Table 1)
Neopentyl glycol diacrylate (SARTOMER SR247 manufactured by Sartomer Americas) (referred to as "SR247" in the following Table 1)
Trimethylolpropane trimethacrylate (NK Ester TMPT manufactured by Shin-Nakamura Chemical Co., Ltd.) (referred to as "TMPT" in the following Table 1)
Ethoxylated (9) trimethylolpropane triacrylate (SARTOMER SR502 manufactured by Sartomer Americas) (referred to as "SR502" in the following Table 1)
Tetraethylene glycol diacrylate (SARTOMER SR268 manufactured by Sartomer Americas) (referred to as "SR268" in the following Table 1)

[Component (C): (Meth)acrylic Monomer Having Acidic Group]
Methacrylic acid (manufactured by Mitsubishi Rayon Co., Ltd.)

[Component (D): Photoinitiator]
2,4,6-Trimethylbenzoyl-diphenyl-phosphine oxide (visible light type photoinitiator) (LUCIRIN (registered trademark) TPO manufactured by BASF SE) (referred to as "TPO" in the following Table 1)
1-Hydroxycyclohexyl phenyl ketone (nonvisible light type photoinitiator) (Suncure 84 manufactured by Chemark Chemical Co., Ltd.) (referred to as "84" in the following Table 1)

[Silane-Based Coupling Agent]
3-Acryloxypropyltrimethoxysilane (KBM-5103 manufactured by Shin-Etsu Chemical Co., Ltd.) (referred to as "5103" in the following Table 1)

[Filler]
Non-treated fumed silica (BET specific surface area: 200 $m^2/g$) (AEROSIL 200 manufactured by NIPPON AEROSIL CO., LTD.) (referred to as "200" in the following Table 1).

The above respective components were blended in the amounts (parts by mass) described in the following Table 1 to prepare a composition. Specifically, the component (A), the component (B) (or the component (B')), the component (C), and the coupling agent were weighed and put in a stirring vessel and stirred while conducting vacuum defoaming for 30 minutes. Thereafter, the filler was weighed and added thereto, and the mixture was further stirred for 30 minutes while conducting vacuum defoaming. Finally, the component (D) was weighed and added thereto, and the mixture was stirred for 30 minutes.

TABLE 1

| Components | Raw materials | Example 1 | Example 2 | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|---|
| Component (A) | UF-8001G | 100 | 100 | 100 | 100 | 100 | 100 | 100 | 100 | 100 | 100 |
| Component (B) | ACMO | 25 | | | | | | | | | 25 |
| | DMAA | | 25 | | | | | | | | |
| Component (B') | 4HBA | | | 25 | | | | | | | |
| | HPMA | | | | 25 | | | | | | |
| | IB-XA | | | | | 25 | | | | | |
| | SR247 | | | | | | 25 | | | | |
| | TMPT | | | | | | | 25 | | | |
| | SR502 | | | | | | | | 25 | | |
| | SR268 | | | | | | | | | 25 | |
| Component (C) | Methacrylic acid | 6 | 6 | 6 | 6 | 6 | 6 | 6 | 6 | 6 | |
| Component (D) | TPO | 4 | 4 | 4 | 4 | 4 | 4 | 4 | 4 | 4 | 4 |
| | 84 | 3 | 3 | 3 | 3 | 3 | 3 | 3 | 3 | 3 | 3 |
| Coupling agent | 5103 | 1 | 1 | 1 | 1 | 1 | 1 | 1 | 1 | 1 | 1 |
| Filler | 200 | 0.4 | 0.4 | 0.4 | 0.4 | 0.4 | 0.4 | 0.4 | 0.4 | 0.4 | 0.4 |
| Sum | | 139.11 | 139.11 | 139.11 | 139.11 | 139.11 | 139.11 | 139.11 | 139.11 | 139.11 | 132.86 |

The respective compositions obtained in Examples 1 and 2 and Comparative Examples 1 to 8 were subjected to the test of durability, confirmation of surface curability, confirmation of heat generation at the time of curing, confirmation of odor, and measurement of shear adhesive force. The results thereof are presented in Table 2. Details of each evaluation are as follows.

[Test of Durability]
The nails of the fingers of human hands were sanded and then the dust and oil were removed from the nails using a solvent for nail exclusive use containing ethanol as a main component. The compositions of Examples 1 and 2 and Comparative Examples 1 to 8 were applied on the surface of the nails using a paintbrush so as to have a thickness of about 300 μm in a wet state. Thereafter, the composition was cured by being irradiated using a nail LED lamp (rated voltage: 240 V 50-60 Hz, power consumption: 30 W, wavelength: 400 to 410 nm) for 10 seconds to obtain a base coat (cured product). A color coat and a top coat were sequentially applied and cured on the base coat by the same method. Super Color EX (color: pastel peach) manufactured by PREGEL was used for the color coat and VL-00 manufactured by VETRO was used for the top coat. The number of fingernails which did not undergo peeling off in 3 weeks after application with respect to the fingernails (10 nails) of the hands of one human was adopted as the "durability (nails/10 nails)". Here, peeling off includes both peeling off from the entire surface and peeling off only from the end portion. It is preferable that the "durability" is preferably 5 or more and more preferably 6 or more when the practicality (applicability as a base coat agent) is taken into consideration.

[Confirmation of Surface Curability]

The compositions of Examples 1 and 2 and Comparative Examples 1 to 8 were applied on an acrylic plate having a thickness of 2.0 mm×a width of 25 mm×a length of 100 mm using a paintbrush so as to have a thickness of about 300 μm in a wet state. The composition was cured by being irradiated using a nail UV lamp (rated voltage: AC 100 V 50 to 60 Hz, power consumption: 36 W, wavelength: 350 to 400 nm) for 60 seconds. The cured state at that time was judged according to the following evaluation criteria, and the judgement was adopted as the "surface curability (UV lamp)".

In addition, the composition applied in the same manner was cured by being irradiated using a nail LED lamp (rated voltage: 240 V 50 to 60 Hz, power consumption: 30 W, wavelength: 400 to 410 nm) for 10 seconds. The cured state at that time was visually judged according to the following evaluation criteria, and the judgement was adopted as the "surface curability (LED lamp)". It is preferable that the surface is cured independently of the kind of lamp, that is, both the "surface curability (UV lamp)" and the "surface curability (LED lamp)" are "○" when the versatility as the base coat agent is taken into consideration:

《Evaluation Criteria》
○: bleeding of components does not occur on surface
X: bleeding of components occurs on surface.

[Confirmation of Heat Generation at Time of Curing]

The compositions of Examples 1 and 2 and Comparative Examples 1 to 8 were applied on the nails of human hands so as to have a thickness of about 100 μm in a dry state and then cured by being irradiated using the nail LED lamp for 10 seconds. The "heat generation at the time of curing" was confirmed according to the following evaluation criteria by the sense of hand at the time of curing. It is preferable that the heat generation at the time of curing is "0" from the viewpoint of securing workability and safety of the subject:

《Evaluation Criteria》
○: subject does not feel that nail is hot
x: subject feels that nail is hot.

[Confirmation of Odor]

The human nose was fixed 10 cm away from the end portion of the container containing the compositions of Examples 1 and 2 and Comparative Examples 1 to 8, and the odor was confirmed by the human sense. The "odor" was confirmed according to the following evaluation criteria. It is preferable that the "odor" is "0" when the influence on the handling person is taken into consideration:

《Evaluation Criteria》
○: odor is not irritating
x: odor is irritating.

[Measurement of Shear Adhesive Force]

The compositions of Examples 1 and 2 and Comparative Examples 1 to 8 were applied between two acrylic plates having a thickness of 2.0 mm×a width of 25 mm×a length of 100 mm in 25 mm×10 mm, and the acrylic plates were pasted to each other. The spilt over composition was removed, and then both ends of the pasted portion were fixed using a jig. This was allowed to pass through a belt conveyor type UV irradiator to be irradiated with UV at an integrated light quantity of 30 kJ/m$^2$, then the jig was removed therefrom, and the composition was irradiated again under the same condition for curing. A test piece containing a cured product of the composition was fabricated by n=5 by this method. The test piece was pulled at a pulling speed of 50 mm/min in the shearing direction by using a universal testing machine, and the strength at the maximum load was adopted as the "shear adhesive force (MPa)" and used as an index of the adhesive force of the cured product to the adherend. The details conform to JIS K6850 (1999). The shear adhesive force in Table 2 represents the average value (n=5) of the shear adhesive forces for the respective test pieces, and it is preferable that the shear adhesive force is 2.5 MPa or more in order to maintain the initial adhesive force.

TABLE 2

| Items of test | Example 1 | Example 2 | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|
| Durability | 5 | 6 | 2 | 3 | 2 | 3 | 0 | 3 | 3 | 3 |
| Surface curability (UV lamp) | ○ | ○ | X | ○ | ○ | ○ | ○ | ○ | ○ | ○ |
| Surface curability (LED lamp) | ○ | ○ | X | ○ | ○ | ○ | ○ | ○ | ○ | ○ |
| Heat generation at time of curing | ○ | ○ | ○ | ○ | ○ | ○ | ○ | X | ○ | ○ |
| Odor | ○ | ○ | ○ | ○ | ○ | X | ○ | ○ | ○ | ○ |
| Shear adhesive force | 3.0 | 3.0 | 3.8 | 3.0 | 3.9 | 3.3 | 1.1 | 3.1 | 2.9 | 2.1 |

When Examples 1 and 2 and Comparative Examples 1 to 8 are compared with each other, the surface curability is "X" in Comparative Example 1, the heat generation at the time of curing is "X" in Comparative Example 6, the odor is "X" in Comparative Example 4, and the shear adhesive force is poor in Comparative Examples 5 and 8. Comparative Examples 1 to 8 were all inferior to Examples 1 and 2 in the durability, and there is a possibility that peeling off occurs in everyday life after the application in the case of Comparative Examples 1 to 8. It is considered that this is because the durability is affected by the moisture remaining at the interface between the nail and the base coat and the moisture remaining at the interface and the temperature by bathing although the factor is not clear. The state of peeling off varies from peeling off of the entire surface to peeling off of the end portion, but it is considered that peeling off occurs from the end portion and then spreads to the entire surface. It is considered that the cured products formed from the compositions of Examples exhibit high toughness and excellent adhesive property at the interface with the nail and thus peeling off hardly occurs at the end portion and favorable durability is exhibited.

INDUSTRIAL APPLICABILITY

The photocurable composition for nail or artificial nail according to the present invention can be used as a photocurable composition for covering nail or artificial nail in accordance with the practice in the field of nails, and specifically, it can be suitably used as a base coat agent on which a top coat and a nail color can be stably applied and thus can be widely used in the field of nails.

Incidentally, the application of the present invention is not limited to the embodiments described above, and the present invention can be appropriately changed without departing from the gist of the present invention.

This application is based upon and claims the benefit of priority of the prior Japanese Patent Application No. 2015-219347 filed on Nov. 9, 2015, the entire contents of which are incorporated herein by reference.

The invention claimed is:

1. A photocurable composition for a nail or artificial nail comprising:
    component (A): a urethane-modified (meth)acrylic oligomer;
    component (B): at least one of 4-acryloylmorpholine or dialkylacrylamide;
    component (C): a (meth)acrylic monomer having an acidic group; and
    component (D): a photoinitiator.

2. The photocurable composition for a nail or artificial nail according to claim 1, wherein the component (A) is a urethane-modified (meth)acrylic oligomer having two (meth)acryl groups in one molecule.

3. The photocurable composition for a nail or artificial nail according to claim 1, wherein the component (B) is contained at from 15 to 50 parts by mass with respect to 100 parts by mass of the component (A) and the component (C) is contained at from 1 to 10 parts by mass with respect to 100 parts by mass of the component (A).

4. The photocurable composition for a nail or artificial nail according to claim 1, wherein the component (C) is (meth)acrylic acid.

5. The photocurable composition for a nail or artificial nail according to claim 1, further comprising a silane-based coupling agent.

6. A method of covering a human nail or an artificial nail, the method comprising applying the photocurable composition for a nail or artificial nail according to claim 1 on a human nail or an artificial nail to form a layer and then irradiating the layer with an energy ray for curing.

7. The photocurable composition for a nail or artificial nail according to claim 1, wherein the photocurable composition for a nail or artificial nail is a base coat agent.

* * * * *